(12) United States Patent
Eigen et al.

(10) Patent No.: US 6,200,818 B1
(45) Date of Patent: Mar. 13, 2001

(54) METHOD FOR DETECTING REACTIONS BY MEANS OF COINCIDENCE ANALYSIS

(75) Inventors: Manfred Eigen; Thorsten Winkler; Jens Stephan; Petra Schwille; Andre Koltermann; Ulrich Kettling; Klaus Dörre; Jan Bieschke, all of Hamburg (DE)

(73) Assignee: Evotec BioSystems AG, Hamburg (DE)

( * ) Notice: Subject to any disclaimer, the term of this patent is extended or adjusted under 35 U.S.C. 154(b) by 0 days.

(21) Appl. No.: 09/581,217
(22) PCT Filed: Dec. 23, 1998
(86) PCT No.: PCT/EP98/08425
   § 371 Date: Jun. 22, 2000
   § 102(e) Date: Jun. 22, 2000
(87) PCT Pub. No.: WO99/34195
   PCT Pub. Date: Jul. 8, 1999

(30) Foreign Application Priority Data

Dec. 23, 1997 (DE) ................................ 197 57 740
Oct. 26, 1998 (DE) ................................ 198 49 265

(51) Int. Cl.[7] ........................................ G01N 21/64
(52) U.S. Cl. ................................ 436/172; 250/459.1
(58) Field of Search ................. 436/164, 172; 250/362, 459.1

(56) References Cited

U.S. PATENT DOCUMENTS 4,395,635 * 7/1983 Friauf et al. ............................ 250/366
4,700,072 * 10/1987 Oikari et al. ............................ 250/328
5,550,382 * 8/1996 Loridon et al. ..................... 250/390.04

FOREIGN PATENT DOCUMENTS

0359681 * 3/1990 (EP) .
0836090 * 4/1998 (EP) .
0884583 * 12/1998 (EP) .

* cited by examiner

Primary Examiner—Jeffrey Snay
(74) Attorney, Agent, or Firm—Jacobson, Price, Holman & Stern, PLLC

(57) ABSTRACT

The invention relates to a method for detecting reactions and conformational changes of analytes in a sample by coincidence analysis, as follows: the sample is marked with at least two different fluorescent dyes and then illuminated with at least one laser in order to stimulate the emission of fluorescence; the fluorescence signals are detected by at least two detection units and each signal is broken down into any simultaneous time segments with the desired time slot widths; the number of signals contained in at least one time segment and/or the time intervals between signals in the time segments are detected; a coincidence analysis of the data detected is carried out for at least one time segment of the first detection unit with at least one isochronous time segment of the second detection unit; statistics are produced showing the results of the coincidence analysis and/or the results are subjected to a threshold value analysis, and these statistics or a combination of more statistics are evaluated for the presence of characteristic features.

13 Claims, 11 Drawing Sheets

METHOD FOR DETECTING REACTIONS BY MEANS OF COINCIDENCE ANALYSIS

The present invention relates to a method for the detection of association, dissociation, linking or cleaving reactions and conformational changes using coincidence analysis.

Finding molecules having specific properties, such as binding, inhibition or catalytic properties, is a key problem in the development of active substance and in biotechnological applications. Molecules having such properties can be either discovered or designed. In this sense, "discovering" means the isolation and screening of substances, while molecular design relies on rational or evolutive techniques. Rational design requires fundamental insights into molecular biophysics to enable prediction of the structure-function relationship. In contrast, in evolutive design, principles of Darwin's Evolution are employed on a molecular level, and new or modified molecules are generated by a combination of mutation, amplification and selection. The use of evolutive techniques in biotechnology, so-called evolutive biotechnology, was proposed by Eigen and Gardiner at the beginning of the 80es (Pure Appl. Chem. 56, 967–978, 1984) and has meanwhile met with a broad acceptance. However, unfortunately, in many evolutive approaches, the process of selection is not immediately linked to amplification. Therefore, selective processes often have to be introduced deliberately. This may be achieved, for example, in the so-called high throughput screening (HTS) in combination with a suitable assay.

HTS processes are subject to economical restrictions. Therefore, to process a large number of samples, it is required for the time to analyze one individual sample to be extremely short. In recent years, many efforts were therefore made in the miniaturization, parallelization and automation of screening techniques and in the development of homogeneous assays and the integration of highly sensitive and quickly operating detection devices. Among the large number of alternative detection principles, techniques based on fluorescence, such as fluorescence resonance energy transfer (FRET), fluorescence quenching, fluorescence polarization, time-resolved fluorescence techniques and fluorescence correlation spectroscopy (FCS), have found a high interest.

In fluorescence correlation spectroscopy, fluorescence fluctuations of individual molecules within a measuring volume element which is in the femtoliter range, in particular, are measured, and molecular diffusion characteristics are established, for example, by evaluating the autocorrelation function of the one-color fluorescence signals. The basics of FCS and its application, in particular, to biological problems have been described in various articles and patent applications (e.g., Eigen and Rigler, Proc. Natl. Acad. Sci. USA 91, 5740–5747, 1994; WO 94/16313).

Fluorescence cross-correlation spectroscopy, or so-called two-color FCS, is also the subject of some publications. Two-color FCS was proposed at the beginning of the 90es by Eigen and Rigler (Proc. Natl. Acad. Sci. USA 91, 5740–5747) and is also discussed in the International Patent Application published under WO 94/16313. Applications of this technology in the study of hybridization kinetics have been described by Schwille et al. (Biophysical Journal, Vol. 72, 1878–1886, 1997). The applications of fluorescence cross-correlation described in the literature show that analysis times of from 30 to 120 s are required to enable a sufficiently precise determination of the amplitudes of the cross-correlation function and the diffusion times. Such long analysis times are not suitable for high throughput screening, or only so in a limited way.

Further, various signal processing methods for separating signals from the background noise have been described in the literature.

Tellinghuisen et al. (Analytical Chemistry 66, No. 1, 64–72, 1994) describes a method for fluorescence lifetime spectroscopy which is intended to serve for filtering out the photons coming from the light source, in this case a laser, from the overall signal. Thus, the current of the signal counter is compared to the trigger signal, i.e., the excitation pulse of the pulsed laser. If a photon arrives simultaneously with the excitation pulse, allowing for the velocity of light, it is identified as a scattering light pulse and eliminated.

Keller et al. (Applied Spectroscopy 50, No. 7, 12–32A, 1996) describes another method for analyzing fluorescence lifetimes. In this method, the time differences between successive, in time, pulses arriving at the detector are determined by counting the number of trigger pulses generated at 100 kHz between two successive photons. These counts are stored in successive channels of an MCS (multichannel scaler). This MCS signal is then subjected to a time-resolved fast Fourier transformation (FFT) for smoothening. After FFT, if at least 5 time differences of the smoothened signal are below a visually determined threshold value, the signal is considered coherent for the whole period of time during which the time differences were continuously below the visually determined threshold value, and evaluated as a fluorescence signal, called "burst" for some time in scientific language. Subsequently, the thus filtered signal is evaluated for fluorescence lifetime. However, the authors only use those signal fractions in which more than 25 time differences are below the visually determined threshold value.

It has been the object of the present invention to provide a method which enables a reliable and fast detection of association, dissociation, linking or cleaving reactions and conformational changes in minute sample volumes.

The object of the invention is achieved by a method having the features of claim 1. The further claims relate to preferred embodiments of the method according to the invention.

Thus, the invention relates to a method for the detection of association, dissociation, linking or cleaving reactions and conformational changes of analytes in a sample using coincidence analysis, wherein the sample contains at least two analytes labeled with different fluorescent dyes, and/or at least one analyte labeled with at least two different fluorescent dyes;

the sample is illuminated by at least one laser for exciting the fluorescence emission of said at least two dyes;

the fluorescent signals emitted by the sample which come from at least one measuring volume element V are detected by at least two detection units;

the signals respectively detected in the detection units or time tracks derived therefrom are cut into arbitrary, but essentially simultaneous, time segments with freely selectable time channel widths;

the number of signals contained in at least one time segment and/or the time intervals between signals within the time segments are established;

for at least one time segment of the first detection unit, a coincidence analysis of the established data with at least one essentially simultaneous time segment of the second detection unit is performed;

at least one statistical analysis of the results of the coincidence analysis is performed, and/or the results are subjected to a threshold analysis;

said statistical analysis or at least one combination of several statistical analyses is evaluated for the presence of properties characteristic of an association, dissociation, linking or cleaving reaction or conformational change.

It may further be preferred that the time channel widths be greater than the longest fluorescence lifetime of said at least two dyes and/or that the time channel widths be smaller than the time required for said at least one sample molecule to pass through the measuring volume.

In a preferred embodiment, the detection units should have different spectral detection sensitivities.

Further, the measuring volume element V should be $\leq 10^{-12}$ l.

It may further be preferred to illuminate the sample with a laser which emits electromagnetic radiation of at least one wavelength which is capable of exciting said at least two dyes present in the sample. However, it is also possible to use lasers which emit more than one wavelength, or to employ several lasers for exciting the fluorescence emission.

It may also be preferred to perform the coincidence analysis on-line and/or to individually adjust the time for performing the respective measurement during the measurement.

It may further be preferred to establish the coincidence in the coincidence analysis by determining the amplitude G(0) of the cross-correlation function.

It may also be preferred to establish the coincidence in the coincidence analysis through a logical AND switching operation.

It may further be desired to establish the coincidence by multiplication according to the following formula:

$$K_i(n) = \frac{\sum_m \prod_j N(m, j)}{\prod_j \sum_m N(m, j)} \cdot n^{(i-1)}$$

wherein N(m,j) is the number of photons in time segment m of detector j; i is the total number of detection units employed; and n is the number of time segments within the time track.

It may also be desirable to move the sample volume and the measuring volume relative to one another.

It may further be preferred to examine systems in which particles occur the molecular weights of which are different by less than a factor of two.

Preferably, the performance of the method according to the invention first comprises the labeling of the sample molecules to be examined by at least two analytes labeled with different fluorescent dyes and/or one analyte labeled with at least two different fluorescent dyes.

The spectrally independent emissions from said at least two different fluorescent dyes are detected in a confocal detection method on independent detectors; preferably, one detector is assigned to each dye. The photon signals produced on the detectors are included by a measuring board simultaneously into as many time tracks as there are detectors and arranged in a grid, preferably in parallel, or simultaneously with freely selectable time channel widths. Thus, synchronized time axes are preferably provided which are divided into freely selectable time channels and in which the photon signals are stored depending on the time of their arrival.

According to the invention, the frequency of signals occurring coincidentally in the synchronized time tracks beyond statistical expectancy is calculated by a suitable algorithm. In a preferred embodiment, this coincidence $K_j$ is calculated by a normalized multiplication, with a freely selectable time resolution, of the i detector channels employed. Thus, preferably, channels with respectively equal time periods of these time tracks of the employed spectrally separated detector channels j=1, . . . , i are multiplied by one another, then the sum of all these products is calculated, which is then normalized and multiplied by the total number n of the time channels or time segments contained in the time track:

$$K_i(n) = \frac{\sum_m \prod_j N(m, j)}{\prod_j \sum_m N(m, j)} \cdot n^{(i-1)}$$

N(m,j) denotes the number of photons in time channel m of detector j; i denotes the total number of detector channels or detector units employed; and n denotes the number of time channels or time segments within the time track.

The value K thus obtained is a possible evaluation criterion for the sample examined. For absolutely independent signals, K=1. If photons are detected simultaneously in said at least two time tracks in a number beyond expectancy, then K>1. The more K exceeds 1, the more coincidences occur in the two time tracks, i.e., the more sample molecules with at least two dyes are detected. FIG. 9 illustrates this measuring principle for a sample which contains two different fluorescent dyes.

Thus, with the method according to the invention, it is not necessary to perform a correlation, which is a fundamental precondition, for example, of one-color FCS. At the same time, the fitting of the measuring curves which is indispensable in FCS has become unnecessary. Further, the amount of data obtained can thus be reduced to the minimum of one value per sample (e.g., $K_2$_1 is directly proportional with the concentration of doubly labeled molecules).

One particularly interesting advantage for the development of homogeneous assays based on the method of the invention is the method's general applicability and flexibility. The target design for conventional one-color FCS, for example, is limited by the necessity of differentiating between positive and negative samples through the diffusion times of the fluorescent molecules. Other fluorescence techniques, such as FRET or fluorescence quenching, are limited in that two fluorophores must be spatially in a suitable mutual proximity. However, they may altogether be suitable for detecting conformational changes. Fluorescence polarization requires a change in the flexibility of the fluorophore for a reaction to be detectable.

Assays based on the method of the invention are not subject to such limitations. The screening for enzymatic activity as well as for inhibitors of enzymatic processes is essentially simplified. Using the principles of evolutive biotechnology in combination with the method according to the invention and novel mutagenesis techniques offers possibilities for the design or optimization of a wide variety of catalytical functions.

Depending on the desired tolerance for false positive or false negative results, it is possible to achieve analysis times of far below 1 s using the method according to the invention. The method according to the invention is a real-time process so that on-line fitting during the measurement becomes possible. In the case of screening for restriction endonuclease activity, most of the samples should usually be negative since a specific enzymatic activity within an arbitrary library is a relatively infrequent event. If a Gaussian function for positive samples is used and a tolerance threshold is established which defines the number of unidentified positive samples in a screening run, a threshold value for the coincidence for clearly negative samples can be defined. All samples having a coincidence value below this threshold value can be directly subjected to another analysis with the same analysis time. Thus, a doubled analysis time results for which a threshold value is again defined. As the distribution functions are separated significnatly better at multiples of this analysis time, most of the false positive samples are identified. Positive samples are subjected to repeated analyses until the desired significance is achieved. Thus, it is possible to perform an adaptive evaluation with analysis times to be defined in each individual case based on a desired level of significance (see, e.g., FIGS. 5 and 8).

The method according to the invention and its embodiments are characterized by the following advantages:

When a two-colored excitation light is generated in only one light source, less expenditure in calibration time is required. This results in an increase in stability with respect to the congruence of the two confocal volume elements. Disturbing wavelengths outside the spectral excitation ranges or within the emission ranges of the two marker fluorophores can be filtered out by suitable optical filters. Adjustment of the relative intensities and beam diameters for both colors can also be effected using suitable filters and pinhole apertures.

One fundamental advantage of the method described is the possibility of very fast characterization. The measuring times achieved to date are within a range of a few milliseconds per sample. For establishing the measured value K, the fundamental lower time limit is the lifetime of the fluorophores employed, which is in contrast to methods such as fluorescence correlation analysis where a limitation is defined by the time which the biomolecules to be examined require for passing through the measuring volume (=diffusion time).

Another advantage of the method of coincidence analysis according to the invention resides in the possibility to evaluate the measured data during data acquisition (on-line) with the aid of a suitable measured value detection/ processing board. In contrast to methods such as fluorescence correlation analysis, mathematical modeling can be dispensed with.

In another preferred embodiment of the method according to the invention, the measuring time is adapted on-line. This adaptive measuring time algorithm enables a further reduction of the total measuring time. Preferably for times which are shorter than the average measuring time required, the unambiguousness of the result is verified. This may be done, for example, by checking whether the coincidence value established at that time can be unambiguously assigned to a particular event, i.e., for example, to a Gaussian distribution for positive or negative samples as shown in FIG. 7 and FIG. 8, respectively. All samples having a coincidence value below or, as the case may be, above a predetermined threshold value can be directly subjected to another analysis. This specification of a particular significance level can also result in a substantial shortening of the measuring time.

Experimental routines for calibrating the system, as necessary, for example, in fluorescence correlation analysis, can also be dispensed with.

In another embodiment, the fluorescence fluctuation necessary for the coincidence analysis is brought about by a controlled movement of the sample molecules relative to the confocal volume. Technically, this is achieved either by moving the sample (application of vibrations of induction of a flux) with stationary optics, or by moving the measuring focus within the stationary sample (confocal scanning), or by a combination of the two. As compared with the fluctuations due to molecular diffusion as usual in FCS, the controlled movement allows for a well-aimed adjustment of the dwelling time of a molecule in the focus as is optimal for fluorescence detection. Thus, the number of fluctuations per unit time can be selectively increased, which leads to a significant enhancement of signal quality. Additional effects result from the increase of the effective measuring volume, which increases the sensitivity of the method, inter alia, and results in a reduction of photobleaching, and from the standardization of the dwelling times in the measuring focus for different molecules, which reduces signal scattering.

The variant of a controlled movement of the sample with stationary optics has been demonstrated by applying vibrations. Thus, the sample holder was mounted on a piezoelectric positioning stage and moved, for example, by oscillations with frequencies of up to 250 Hz within the plane perpendicular to the optical axis. Already at frequencies of between 100 and 200 Hz, a significantly increased signal-to-noise ratio resulted with a concomitant reduction of the measuring time required for evaluation.

It could also be shown that the width in time of the time channels and the frequency of the periodic relative motions can beneficially influence the measuring values. It was found (FIG. 10) that the time channel width should preferably be selected greater than the triplet lifetime of the fluorophores and/or smaller than the average time required for the molecules to pass through the measuring volume.

Another fundamental advantage of the method of coincidence analysis according to the invention is the possibility to also examine systems in which particles occur the molecular weights of which are different by less than a factor of two. Examining such systems, for example, with fluorescence correlation analysis, in which the diffusion times are determined, leads to problems with the ambiguity of the differentiation. In contrast, in the method according to the invention, an unambiguous, differentiation is possible by determining the coincidence between time tracks of spectrally separated detectors.

In another embodiment of the method according to the invention, the coincidence can also be detected by determining the amplitude G(0) of the cross-correlation function. The amplitude G(0) is sufficient for obtaining results about the concentration of the molecule to be examined an thus, for example, for determining the activity of a restriction endonuclease, as illustrated in Example 1 and in FIG. 5.

In another embodiment, the coincidence analysis can also be realized by a logical AND or multiplication element on the hardware level.

In addition, the substrate concentration can also be reduced down to the subpicomolar range with the method according to the invention.

Figure 3:
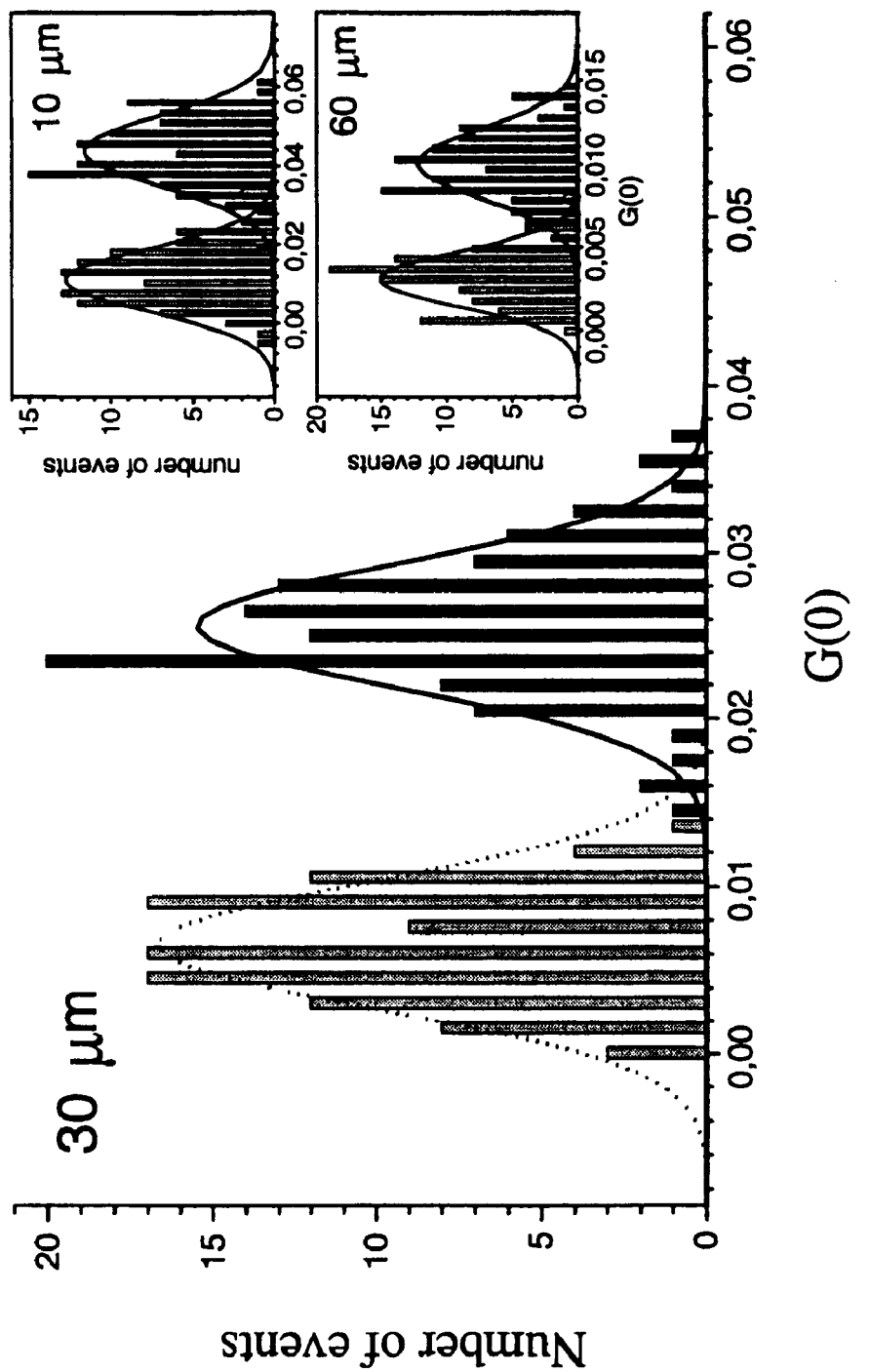

The histograms illustrated in FIG. 3 show the distributions of the evaluated cross-correlation amplitudes G(0) obtained from samples with or without restriction endonuclease activity using pinhole apertures of different diameters.

Figure 4:
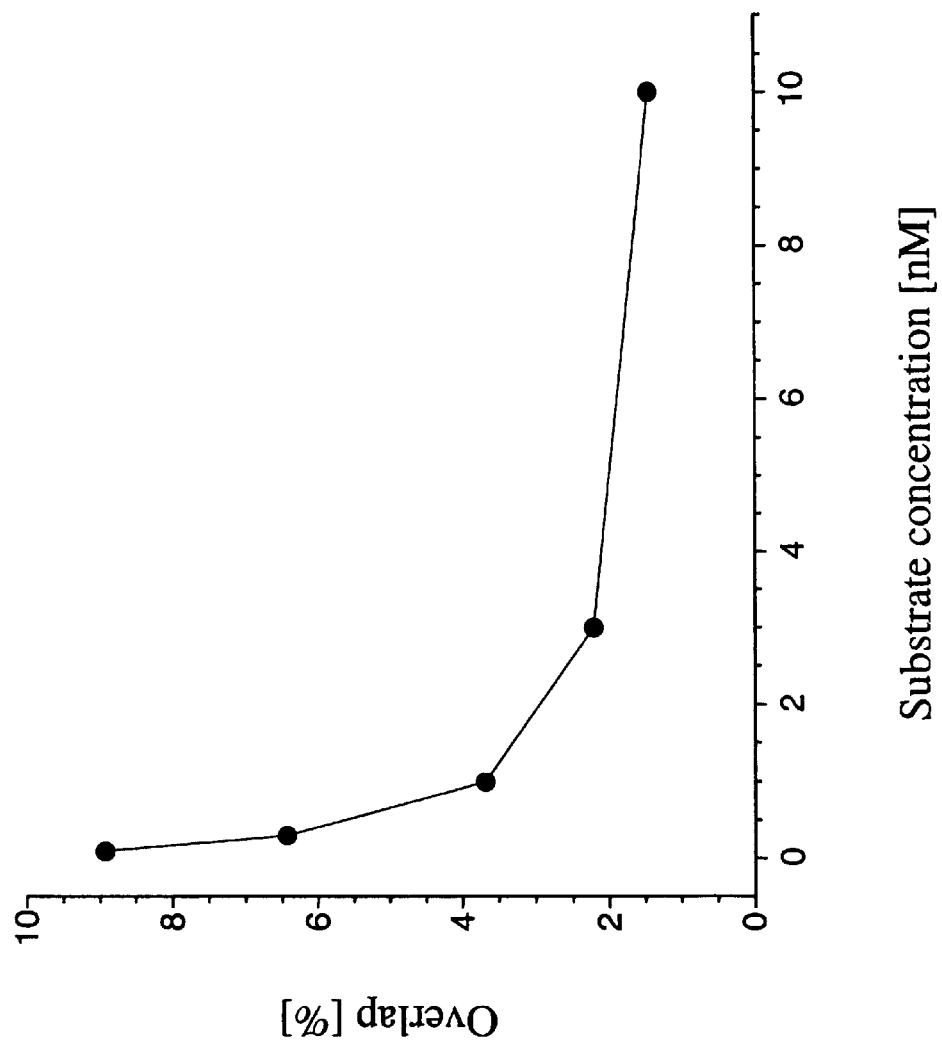

FIG. 4 illustrates the influence of substrate concentration on the overlap between the distribution functions of samples with or without enzymatic activity.

Figure 5:
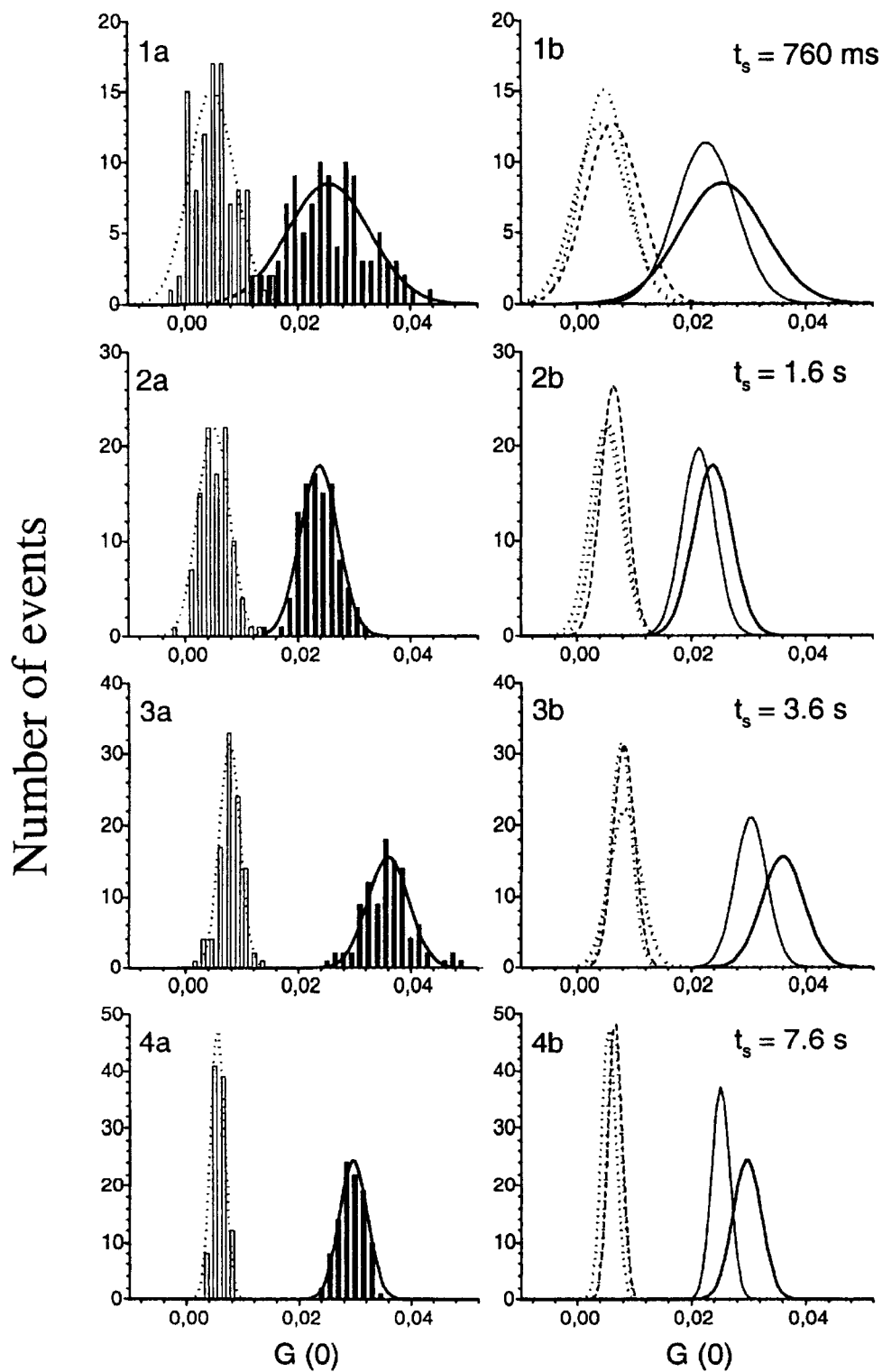

FIG. 5 shows the application of the method according to the invention to a simulated high throughput screening for restriction endonuclease activity with determination of the parameter G(0).

Figure 6:
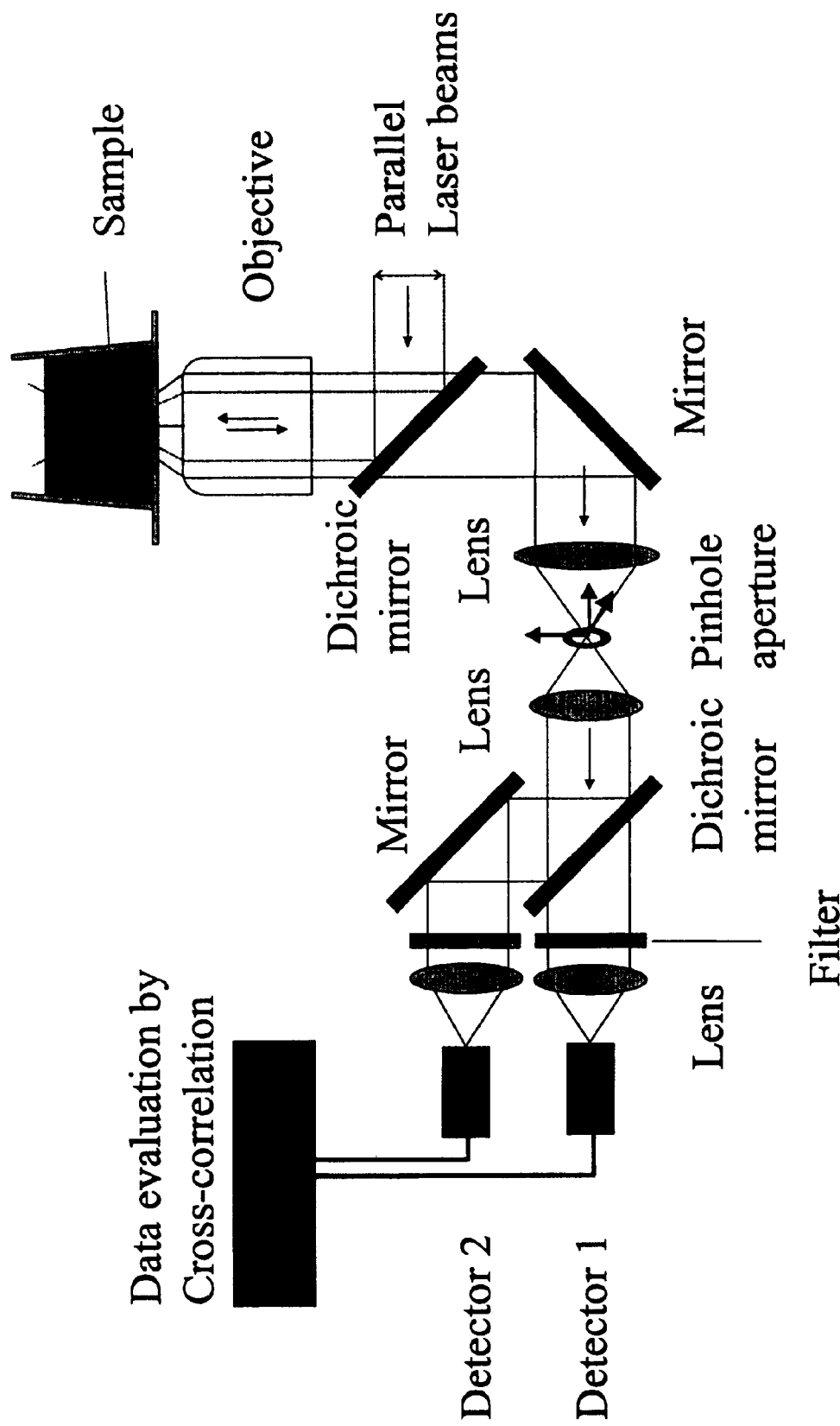

FIG. 6 illustrates a preferred embodiment of the optical configuration using a two-color fluorescence cross-correlation spectrometer.

Figure 7:
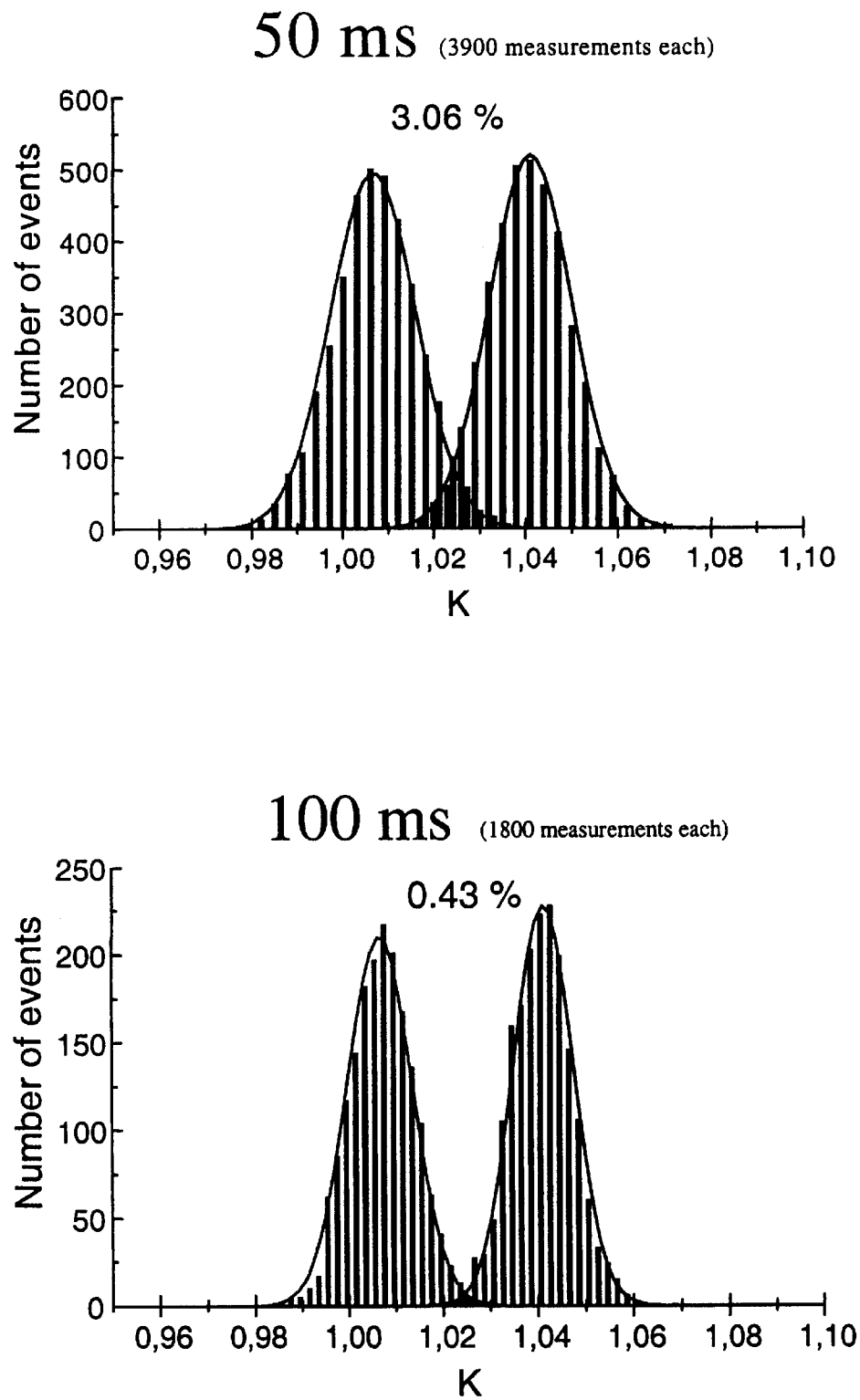

FIG. 7 shows how the measuring times can be significantly reduced by the method according to the invention.

Figure 8:
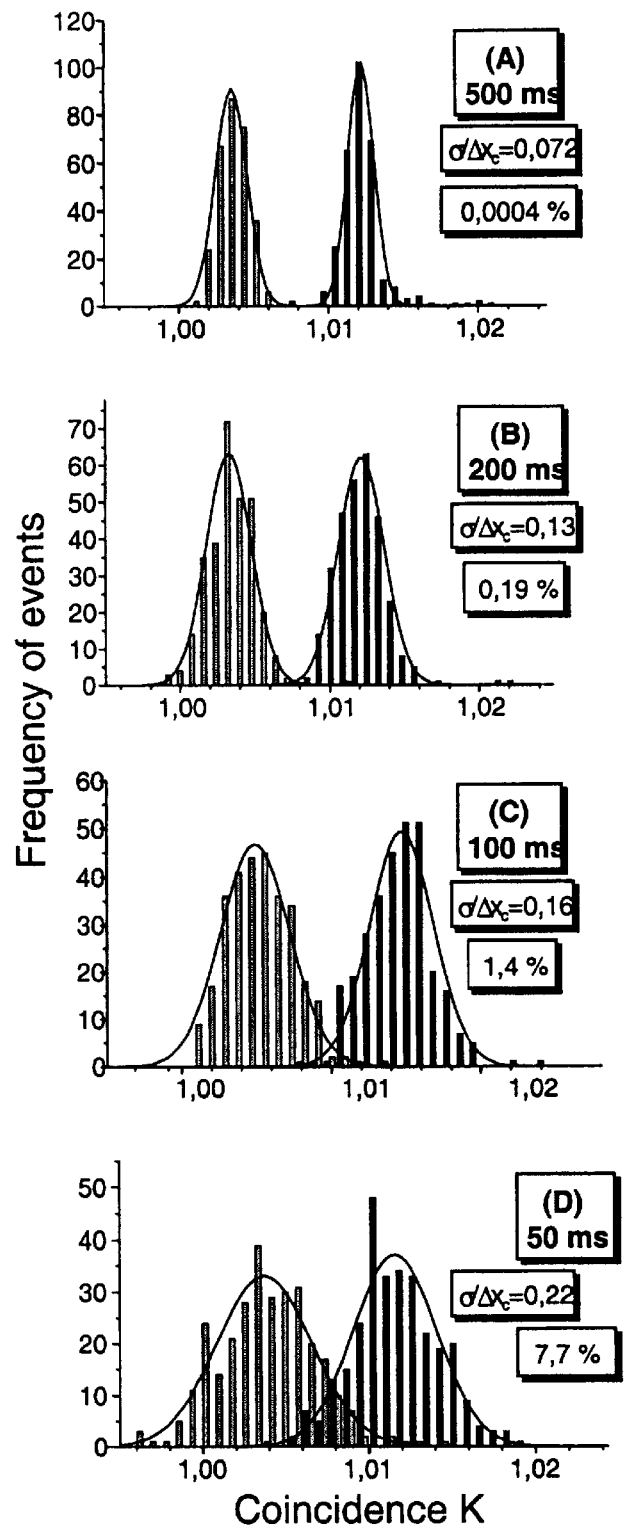

FIG. 8 shows the influence of the measuring time on the overlap between the distribution functions of samples with or without enzymatic activity.

Figure 9:
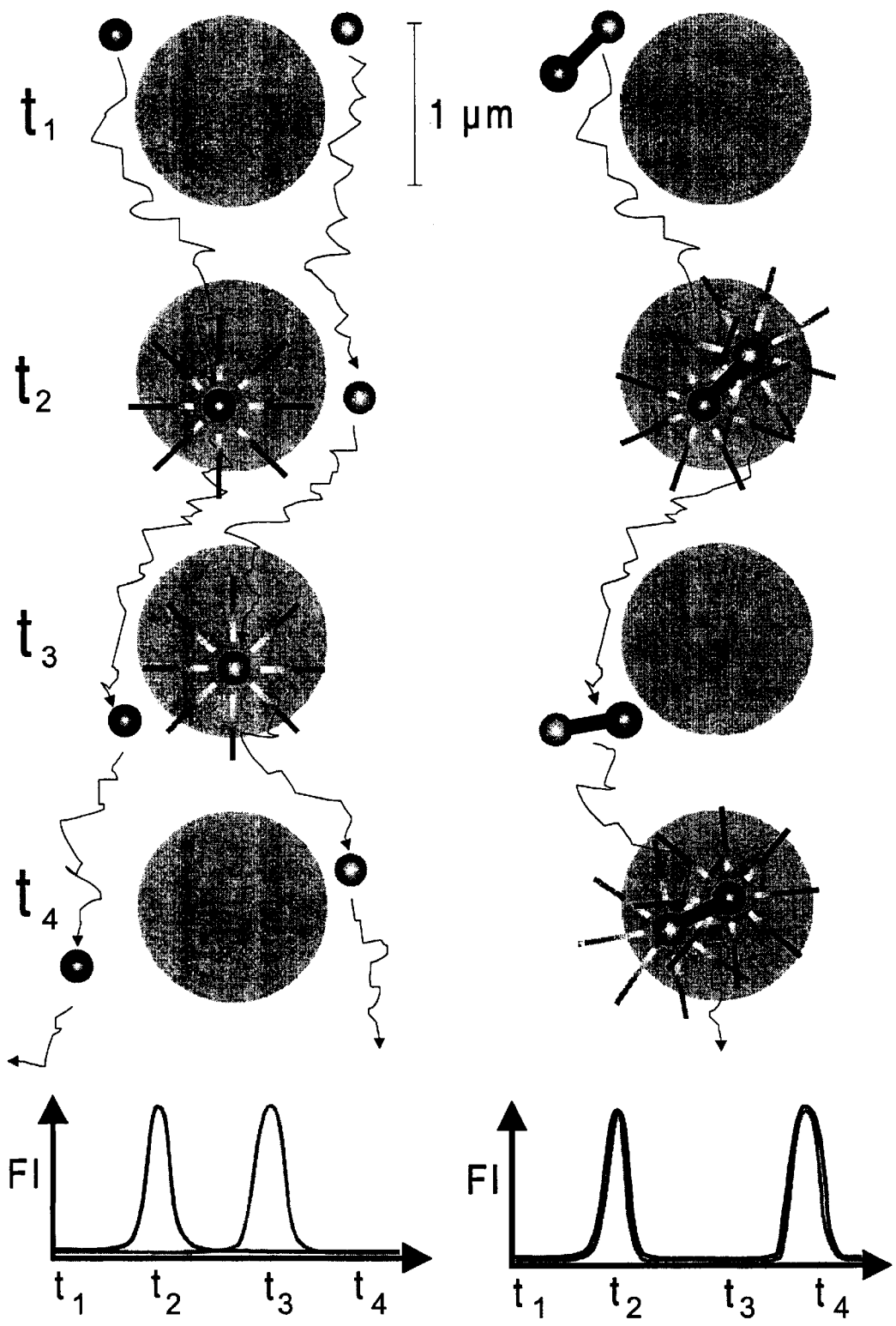

FIG. 9 schematically shows a measuring principle.

Figure 10:
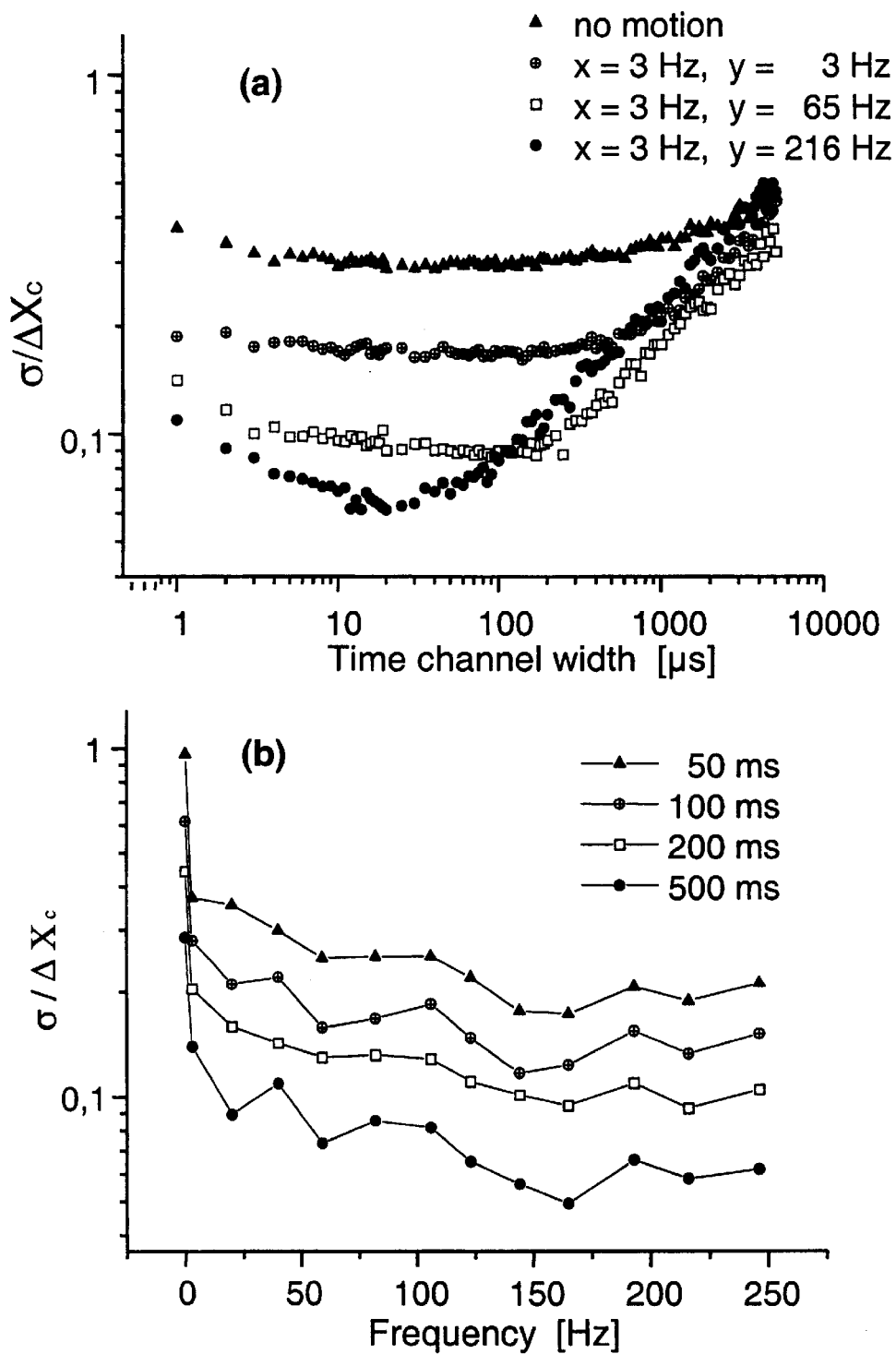

FIG. 10 shows the significance to coincidence analysis of the width in time of the time channels and the frequency of the periodic relative motion.

Figure 11:
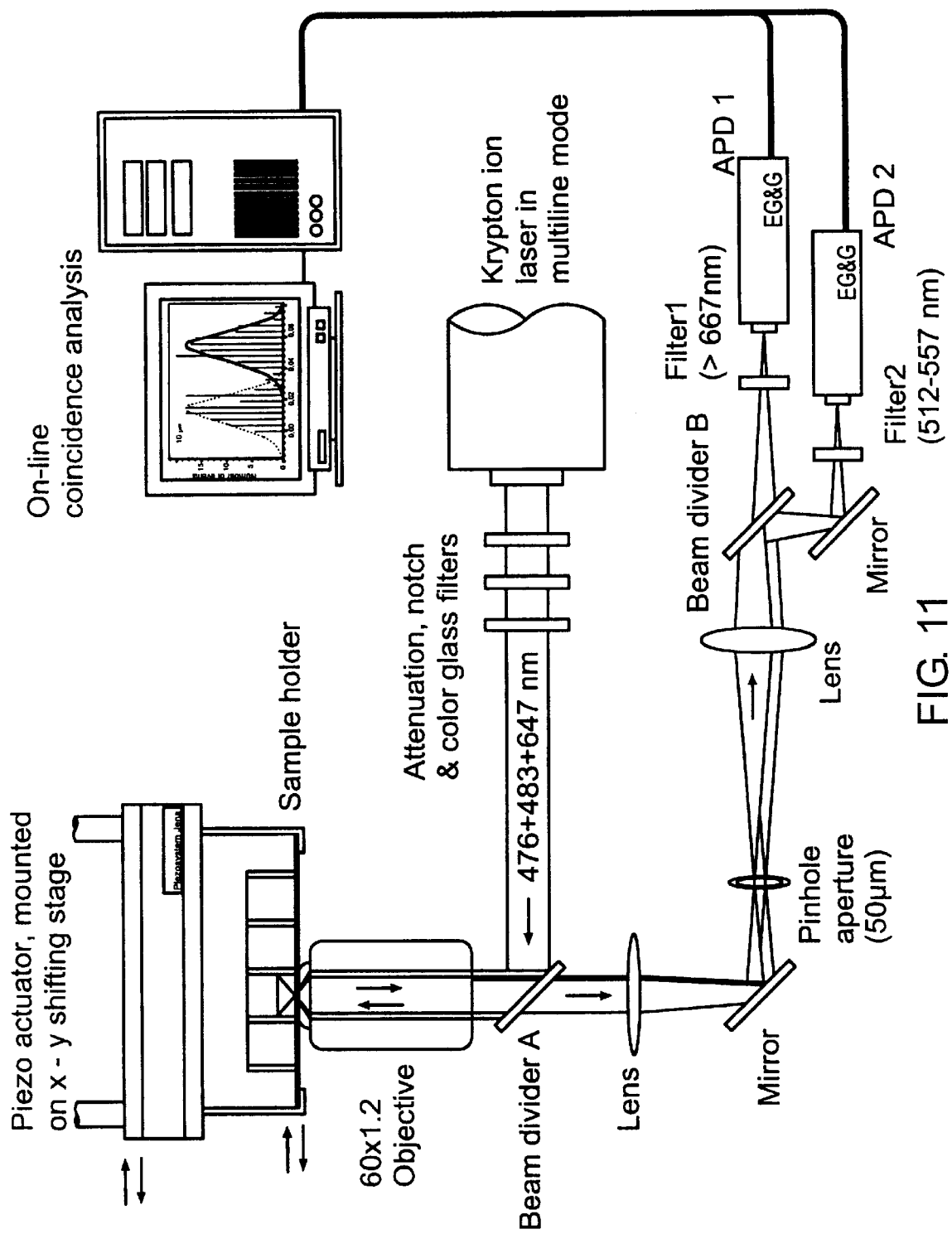

FIG. 11 illustrates a preferred embodiment of the optical configuration with a device for moving the sample by applying vibrations.

Figure 1:
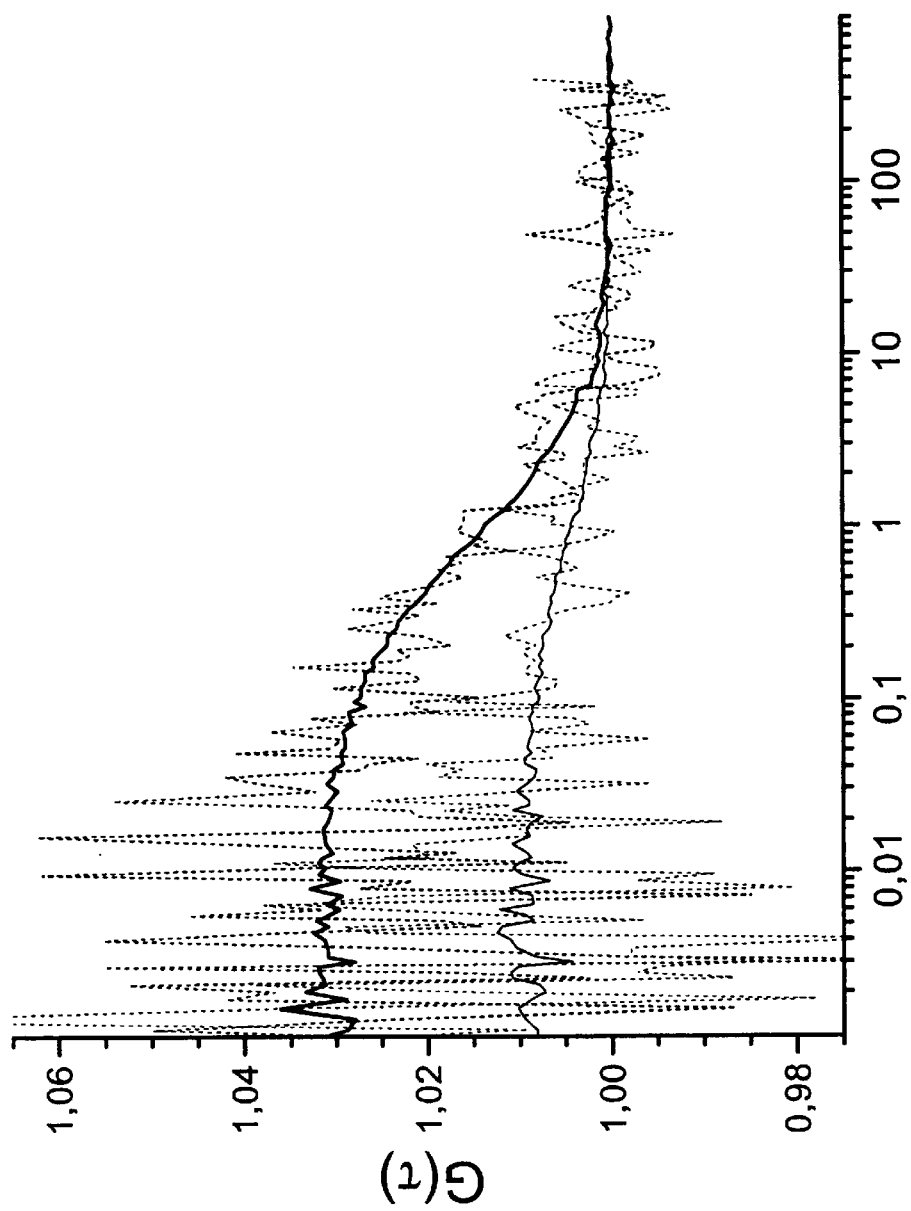
FIG. 1 shows typical cross-correlation curves obtained from samples with or without restriction endonuclease activity with different analysis times.

FIG. 1 shows typical cross-correlation curves obtained from samples with or without restriction endonuclease activity with different analysis times. The assays were performed using 10 nM labeled DNA substrate which was incubated for 3 hours at 37 ° C. with 0.25 U/$\mu$l of EcoRI (lower thin lines) or without the addition of an enzyme (upper lines in boldface). The correlation times were 760 ms (dotted lines) and 120 s (solid lines). The pinhole aperture employed had a diameter of 30 $\mu$m. The excitation intensities were 19 kW/cm$^2$ (488 nm) and 15 kW/cm$^2$ (633 nm). The cross-correlation curve obtained at shorter analysis times includes more noise than the cross-correlation curve obtained at long analysis times. Nevertheless, the characteristic diffusion times and particle counts are sufficiently in agreement to allow for the statement that the curves obtained contain the same information.

Figure 2:
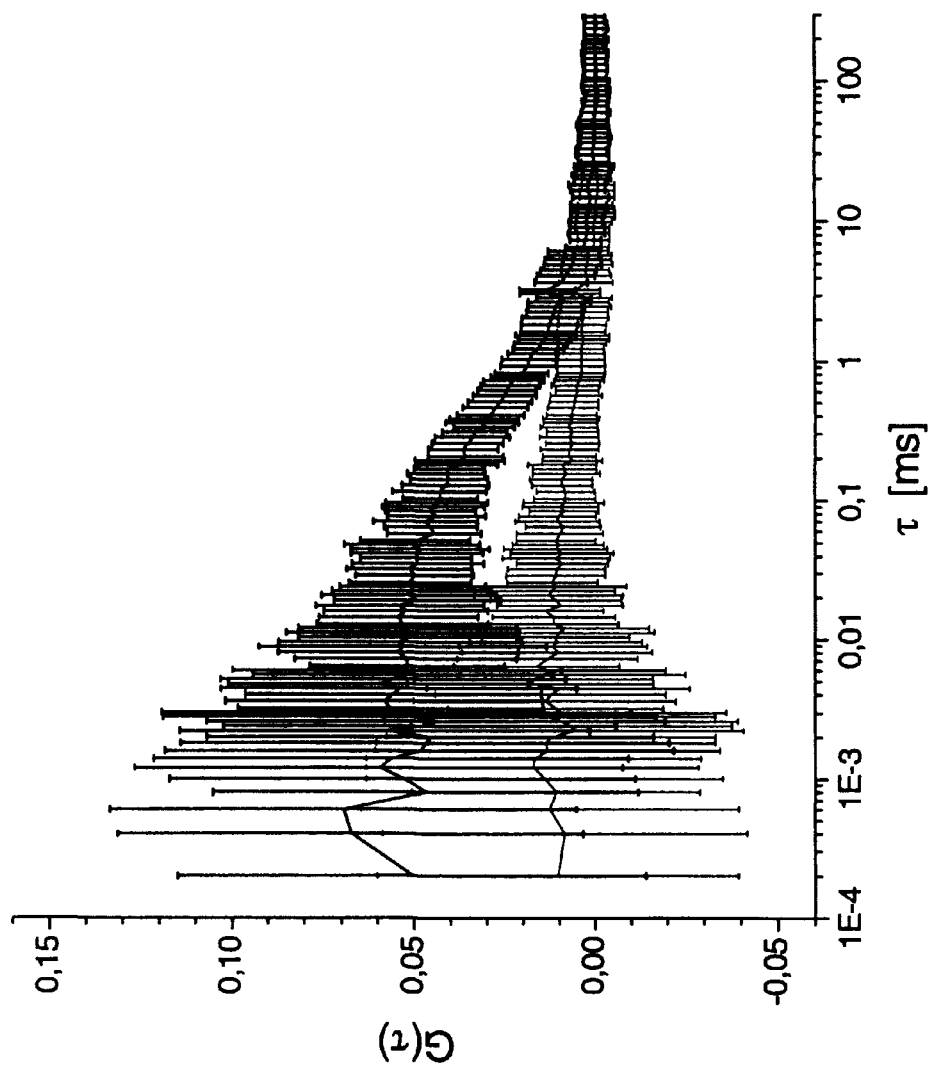
FIG. 2 shows the average values of the respective individual cross-correlation points and their standard deviations, obtained from samples with or without restriction endonuclease activity.

FIG. 2 shows the average values of the respective individual cross-correlation values $\tau$ and their standard deviations, obtained from samples with or without restriction endonuclease activity. The assays were performed using 1 nM labeled DNA substrate which was incubated for 3 hours at 37° C. with 0.25 U/$\mu$l of EcoRI (lower thin line) or with 0.25 U/$\mu$l of HindIII (upper line in boldface). The correlation times were 1.6 s. The pinhole aperture employed had a diameter of 30 $\mu$m. The excitation intensities were 38 kW/cm$^2$ (488 nm) and 31 kW/cm$^2$ (633 nm). It was found that the standard deviations are drastically increased for $\tau$ values of below 0.01 ms.

The histograms illustrated in FIG. 3 show the distributions of the evaluated cross-correlation amplitudes G(0) obtained from samples with or without restriction endonuclease activity using pinhole apertures of different diameters. The bars indicate the number of G(0) values within a bin width of 0.0015 (30 $\mu$m), 0.0026 (10 $\mu$m) or 0.00062 (60 $\mu$m). The main part of the picture shows the distribution functions of samples with (dotted bars) or without (solid bars) enzymatic activity for the optimum diameter of the pinhole aperture (30 $\mu$m); the overlap between the Gaussian curves is 0.6%. It is 2.4% for a diameter of the pinhole aperture of 10 $\mu$m and 3.4% for a diameter of the pinhole aperture of 60 $\mu$m. The assays were performed formed using 10 nM labeled DNA substrate which was incubated for 3 hours at 37° C. with 0.25 U/$\mu$l of EcoRI (dotted bars) or with 0.25 U/$\mu$l of HindIII (solid bars). The correlation times were 1.6 s. The excitation intensities were 38 kW/cm$^2$ (488 nm) and 31 kW/cm$^2$ (633 nm). The established optimum diameter of the pinhole aperture evidently reflects a compromise between the increase of detection efficiency with increasing diameter of the pinhole aperture (due to an increased dwelling time of the fluorophores in the focus) and the decrease of the signal-to-noise ratio with increasing diameter of the pinhole aperture (due to an increased fluorescence background).

FIG. 4 illustrates the influence of substrate concentration on the overlap between the distribution functions of samples with or without enzymatic activity. The assays were performed as described in the legend for FIG. 3 using a diameter of the pinhole aperture of 30 $\mu$m. The separation of the distribution functions increased with increasing concentration.

FIG. 5 shows the application of the method according to the invention to a simulated high throughput screening for restriction endonuclease activity. The samples were screened cyclically (for a total of 500 measurements). The left-hand portion of FIG. 5 shows the distribution functions of samples with (BamHI, open bars) and without (HindIII, solid bars) specific endonuclease activity for analysis times of 760 ms (1a), 1.6 s (2a), 3.6 s (3a) and 7.6 s (4a). The distribution functions of the cross-correlation amplitudes G(0) were evaluated as described in the legend for FIG. 3. The bin width was 0.0015. The right-hand portion of FIG. 5 illustrates the separation efficiency of the method according to the invention by Gaussian fitting for pure substrate (solid line), HindIII (solid line in boldface), BamHI (dotted line in boldface), EcoRI (dotted line) and SspI (dashed line). The overlap was 2.6–5.4% (760 ms), 0.1% (1.6 s), <0.002% (3.6 s) and <<10$^{-5}$% (7.6 s). The assays were performed in a volume of 5 $\mu$l using 10 nM labeled DNA substrate which was incubated for 3 hours at 37° C. with 0.25 U/$\mu$l of HindIII, 0.1 U/$\mu$l of BamHI, 0.25 U/$\mu$l of EcoRI, 0.08 U/$\mu$l of SspI, or without addition of an enzyme. The excitation intensities were 19 kW/cm$^2$ (488 nm) and 15 kW/cm$^2$ (633 nm). The diameter of the pinhole aperture was 30 $\mu$m. It is found that as the analysis time increases, the distribution functions became narrower, and thus the mean values can be clearly separated.

FIG. 6 shows the optical configuration of a two-color fluorescence cross-correlation spectrometer. Two parallel laser beams of an argon ion laser (488 nm) and a helium neon laser (633 nm) pass a water-immersion objective (40x, n.a.=1.2) in an epi-illumination arrangement so that the two superimposed foci form a confocal volume element on the order of femtoliters in the sample. The emitted-fluorescent light is collected by the microscope objective, separated from the excitation light path by a dichroic mirror, and focused onto a pinhole aperture by a lens. The pinhole aperture of variable diameter is provided in the image plane of the lens and can be adjusted in x, y and z directions. The fluorescent emission is made parallel, separated into green and red fractions by a dichroic mirror, and refocused onto two avalanche photodiodes.

In FIG. 7, a variant of the method according to the invention was introduced which was used for a controlled movement of the sample with stationary optics by applying vibrations. Thus, the sample holder was mounted onto a piezoelectric positioning stage and appropriately oscillated. Samples were used which contained 10 nM of double-stranded DNA substrate and to which, in one embodiment, restriction endonuclease EcoRI was further added or, in another embodiment, no such enzyme was added. The upper portion of the Figure shows that at an analysis time of 50 ms (3900 measurements each, frequencies of 75 Hz (x) and 49 Hz (y)), an overlap between signals of the two different sample types of about 3% could be achieved. In the lower portion of the Figure, it is seen that at an analysis time of 100 ms (1800 measurements each, frequencies of 75 Hz (x) and 49 Hz (y)), an overlap of even only 0.4% could be achieved. Thus, it is clearly shown that a shortening of the measuring time and an increased data accuracy can be achieved by applying a forced movement to the fluorescent particles.

FIG. 8 shows histograms from 300 measurements each of the coincidence value for samples of pure substrate (10 nM of doubly labeled double-standard DNA, solid bars) and a sample already restricted by endonuclease (10 nM of doubly labeled double-stranded DNA, dotted bars) at an oscillation frequency of 216 Hz. FIGS. A–D show different analysis times. The distributions were fitted to a Gaussian function. For determining the measuring error, the standard deviations and the overlap of the fitting functions were determined.

FIG. 9 schematically illustrates a measuring principle. In the left column, different dyes independently diffuse through the sample solution. The occurrence of each dye in the measuring volume is therefore independent of the behavior of the other dye, and the photon events in a time track are statistic in nature and completely independent of the photon events recorded in the other time track. The coincidence value in such a case is exactly K=1. In the right column, both dyes are linked to each other and now diffuse together through the sample solution. When the complex appears in the measuring volume, photon events are simultaneously (i.e., in the same time channel m) recorded in the two measuring tracks. This mutual dependence of the signals from the independent, spectrally separated detectors leads to an accumulation of coincidences (i.e., simultaneously recorded photons) which goes beyond the statistical expectancy for independent signals. The coincidence value in such a case is K>1. The higher the content of different mutually linked dyes, the more K is different from 1.

FIG. 10 represents the detection certainty as a function of the width in time of the time channels (a) and the periodic relative motion (b) to which the sample and measuring volumes are subjected. In order to determine suitable ranges for the values of these parameters, a test sample was used (10 nM dsDNA doubly labeled with the dyes rhodamine green and Cy-5), and 300 independent measurements each were performed for various combinations of values with a measuring time of 500 ms each. In order to correctly characterize the measure for the detection certainty of a sample with doubly labeled molecules, the relative standard deviation $\sigma/\Delta x_c$ was derived from the fitted Gaussian distribution. It indicates the ratio of the standard deviation a to the distance Axc between the center of the distribution (Xc) and the center which a distribution would have if it described a measuring sample without any doubly labeled molecules ($X_{c,0}=1$). A low means a small overlap between a "positive" distribution and a "negative" distribution and thus increased detection certainty. In FIG. 10(a), $\sigma/\Delta x_c$ is plotted for different widths in time of the time channels. A plateau of minimum relative standard deviation forms at medium values of the time channel width. For time channel widths which are in the range of the triplet state lifetime of the dye molecules (<5 $\mu$s), $\sigma/\Delta x_c$ increases. Similarly, $\sigma/\Delta x_c$ increases if the time channel width reaches into the range of the average time required for the molecules to pass through the measuring volume. However, when the frequency of the relative motion is increased, this upper limit of the time channel widths can be lowered. FIG. 10b shows the dependence of the relative standard deviation $\sigma/\Delta x_c$ on the frequency of the relative motion between the sample volume and the measuring volume. (The y frequency is always indicated. Unless it is zero, it is always accompanied by a frequency of 3 Hz in x direction.) Curves for different measuring times are plotted, the channel width being 12.5 $\mu$s. Even at a low frequency of the relative motion, a very steep drop of the relative standard deviation can be seen. The course of the curve shows a moderate reduction of $\sigma/\Delta x_c$ as the frequency increases. In the range of 3–246 Hz, $\sigma/\Delta x_c$ is again reduced by a factor of about 2, and further improvements are to be expected when even higher frequencies are applied. The relative standard deviations decrease as the measuring time increases.

FIG. 11 shows the optical configuration of a two-color fluorescence cross-correlation spectrometer with a device for moving the sample by applying vibrations. Parallel laser beams of a krypton ion laser with wavelengths of 476/483 nm and 647 nm pass a water-immersion objective (60x, n.a.=1.2) in an epi-illumination arrangement. The sample holder is connected with a two-dimensionally movable piezo actuator which is again mounted on a mechanical high-precision x-y shifting stage. The emitted fluorescent light is collected by the microscope objective, separated from the excitation light path by a dichroic mirror, and focused onto a pinhole aperture by a lens. The pinhole aperture of variable diameter is provided in the image plane of the lens and can be adjusted in x, y and z directions. The fluorescent emission is made parallel, separated into green and red fractions by a dichroic mirror, and refocused onto two avalanche photodiodes.

EXAMPLE 1

Materials employed:

Type II restriction endonucleases (E.C. 3.1.21.4) EcoRI (25 U/$\mu$l), BamHI (10 U/$\mu$l), SspI (8 U/$\mu$l) and HindIII (25 U/$\mu$l) were supplied by Stratagene (La Jolla, Calif.); the enzyme activities are given in parentheses. The fluorescence-labled 66 bp oligonucleotides Cy5-ATGGCTAATGACCGAGAATAGGATCCGAA TTCAATT GGTACCTACGGGCTTTGCGCTCGTATC and RhG-
GATACGAGCGCAAAGCCCGTAGGTAC-
CQAAATTTGAATTCGATCCCTAT
TCTCGGTCATTAGCCAT
were synthesized by MWG Biotech (Ebersberg, Germany) and purified by HPLC; the first oligonucleotide has Cy5 as a fluorescent marker at the 5' terminus (Amersham, UK) while the second oligonucleotide is labeled with rhodamine green RhG (Molecular Probes). Hybridization of the two complementary strands results in recognition sites for BamHI (single underlining), EcoRI (double underlining) and SspI (dotted). The hybridization of the complementary strands was effected at concentrations of 1 $\mu$M in 100 mM KOAc, 25 mM tris-acetate, pH 7.6, 10 mM MgOAc, 0.5 mM β-mercaptoethanol, 10 $\mu$g/ml BSA with heating the solution to 94° C., followed by cooling to 23° C. with a temperature gradient of 1.2° C./min. The result was a doubly labeled DNA double strand with recognition sites for BamHI, EcoRI and SspI.

Homogeneous restriction endonuclease assay:

Endonuclease assays were performed at 37° C. for 3 hours. The reaction buffer contained 150 mM KOAc, 37.5 mM tris-acetate, pH 7.6, 15 mM MgOAc, 0.75 mM β-mercaptoethanol, 515 $\mu$g/ml BSA, 0.05% Triton X-100, 0.5% glycerol, 1–20 nM labeled DNA substrate and excess proportions (0.08–0.25 U/$\mu$l) of restriction enzymes BamHI, EcoRI, SspI and HindIII.

Optical configuration:

The measurements were made using a two-color fluorescence cross-correlation spectrometer (Dual-color ConfoCor, C. Zeiss, Oberkochen, Germany). The confocal measuring volume of 0.44 fl was formed by superimposing the foci of an argon ion laser (488 nm) and a helium neon laser (633 nm). The fluorescence emission signals are separately detected using two avalanche photodiodes; a confocally arranged pinhole aperture was provided in the emission light path. The spectrometer was equipped with a thermostat. The focus was positioned 100 µm above the bottom of the respective sample vessel. The measuring temperature was 22° C. The samples were provided in sample holders in a microtitration plate format. These were either plastic sheets sealed in a contamination-free manner (Max-Planck-Institut fur Biophysikalische Chemie) or commercial cover slide chambers (Nunc, Denmark).

Cross-correlation analysis

The theoretical background of cross-correlation analysis has been described in detail by Schwille et al. (Biophys. J. 72, 1878–1886, 1997), the disclosure of which is incorporated herein by reference. The data of cross-correlation were evaluated using a three-dimensional model for individual diffusing particles (Rigler and Widengren, Bioscience 3, 180–183, 1990):

$G(0)$ designates the correlation amplitude at $\tau=0$, which is proportional with the concentration of doubly labeled molecules in the cylindrical measuring volume of a radius $r_0$ and a half length of $z_0$. According to the equation $\tau_{Diff}=r_0^2/4D$, the parameter $\tau_{Diff}$ is in an inversely proportional relationship with the diffusion coefficient D. The experimental data were processed using the Access 2.0 Program by EVOTEC BioSystems GmbH by means of non-linear least-squares Marquardt fitting. $G(0)$ was the only free parameter in the evaluation of the cross-correlation measurements. The structural parameter $z_0/r_0$ was established by autocorrelation measurements on a free dye solution; the average diffusion time $\tau_{Diff}$ of the substrate was determined mined by a 60 s measurement without the addition of enzyme. Both parameters were preset in the fitting of the cross-correlationcorrelation data.

Statistical evaluation:

A typical set of cross-correlationcorrelation measurements contained 100 curves which were recorded using accumulation times of between 760 ms and a few seconds. From each set, the amplitude $G(0)$ obtained by fitting was plotted in a histogram (for details see FIG. 3). The analysis showed that the $G(0)$ distribution functions can be approximated by a Gaussian function. The mean values of the Gaussian functions correspond to the average concentrations of the fluorophores while the standard deviations reflect the scatter of the individual measurements. To obtain a measure of the distinguishability of the distribution functions, the overlap area of the fitted Gaussian functions was established by integrating the Gaussian functions. The overlap areas were normalized so that 100% overlap corresponds to Gaussian functions with identical mean values and identical standard deviations.

EXAMPLE 2

Materials employed:

The materials employed and experimental conditions essentially corresponded to those stated in Example 1. However, only EcoRI was used as a restriction endonuclease.

Homogeneous restriction endonuclease assay:

The endonuclease assays for EcoRI were performed in accordance with Example 1. A sample to which no restriction endonuclease had been added was used as a reference.

Optical configuration:

The experimental design is represented in FIG. 11. The fluorescence excitation was effected by epi-illumination of a water-immersion objective (UPLAPO 60x/1.2 W; Olympus, Japan) with the wavelengths 476/483 nm and 647 nm of a krypton ion laser (INNOVA 90-K; Coherent, Palo Alto, USA) operated in a multiline mode. The dichroic beam divider A (AHF Analysentechnik, Töbingen) reflects at <502 nm and 585–655 nm and transmits at 502–585 and >655 nm. Additional laser lines at 531 nm and 568 nm are eliminated with a specially prepared excitation/notch filter (>OD 5; AHF Analysentechnik). Balanced relative laser excitation energies for both wavelengths are obtained by the combination of a color glass absorption filter (BG 40, Andover Corporation, Salem, USA) and an attenuation filter (OD 0.6; Spindler & Hoyer, Göttingen). The samples were provided in commercial cover slide chambers (Nunc, Denmark). The sample holder is connected with a two-dimensionally movable piezo actuator (Piezosystem Jena) which is again mounted on a mechanical high-precision x-y shifting stage (Märzhauser, Wetzlar). The fluorescent photons are spectrally separated at the dichroic beam divider B (585DCLP02; Omega Optical, Brattleboro, USA) and imaged on two avalanche photodiodes (APD) (SPCM-AQ 131-FS; EG&G Optoelectronics, Canada) after optical filtering in the red (667EFLP; Omega) and green (535RDF45; Omega) channels. The digital pulses from the APDs are recorded either by a Dual Input Multiscaler PC board (MCD, FAST ComTec, Munich) for the analysis of time tracks with high temporal resolution, or by an on-board processor PC board (Adwin-LD; Jäger Messtechnik, Lorsch), which can be programmed for on-line data processing.

Coincidence analysis:

To establish the coincidence, the photon counting signals of the two detectors were simultaneously recorded by a measuring board and simultaneously arranged in a grid with a selectable time channel width. Of the thus obtained two time tracks, channels with respectively equal time periods are multiplied by one another, then the sum of all products is calculated and divided by the two time track (individual) sums for normalization and multiplied by the total number of the time channels:

$$K(n) = \frac{\sum_m N_1(m)N_2(m)}{\sum_m N_1(m) \sum_m N_2(m)} \cdot n$$

wherein m denotes the index of the respective time channel (in the order of elapsing time), n denotes the total number of the time channels contained in a time track, $N_1(m)$ denotes the number of photon counts in time track 1 in time channel m, and $N_2(m)$ denotes the number of photon counts in time track 2 in time channel m.

Evaluation

The value K obtained is the evaluation criterion for the sample under consideration. Only the number of coincident events is evaluated. For totally independent signals, K is 1 because of the normalization. If photon signals occur in both time tracks simultaneously in a frequency beyond statistical expectancy, then K>1. The higher K is above 1, the more coincidences, i.e., simultaneously recorded photons, occur in the two time tracks. The latter number is a measure of the fraction of molecules to which both dye species are bound.

Statistical evaluation:

A statistical analysis of the coincidence values was also made.

The coincidence values established in 300 measurements each on samples of pure substrate and 300 measurements each on samples already restricted by endonuclease at an oscillation frequency of 216 Hz and different analysis times were plotted in a histogram (see FIG. 8). The analysis showed that the coincidence values can be approximated by a Gaussian function. The mean values of the Gaussian function less one correspond to the average concentrations of doubly labeled substrate while the standard deviations reflect the scatter of the individual measurements. To obtain a measure of the distinguishability of the distribution functions, the overlap area of the fitted Gaussian functions was established by integrating the Gaussian functions. The overlap areas were normalized so that 100% overlap corresponds to Gaussian functions with identical mean values and identical standard deviations.

What is claimed is:

1. A method for the detection of association, dissociation, linking or cleaving reactions and conformational changes of analytes in a sample using coincidence analysis, wherein
    the sample contains at least two analytes labeled with different fluorescent dyes, and/or at least one analyte labeled with at least two different fluorescent dyes;
    the sample is illuminated by at least one laser for exciting the fluorescence emission of said at least two dyes;
    the fluorescent signals emitted by the sample which come from at least one measuring volume element V are detected by at least two detection units;
    the signals respectively detected in the detection units or time tracks derived therefrom are cut into arbitrary, but essentially simultaneous, time segments with freely selectable time channel widths;
    the number of signals contained in at least one time segment and/or the time intervals between signals within the time segments are established;
    for at least one time segment of the first detection unit, a coincidence analysis of the established data with at least one essentially simultaneous time segment of the second detection unit is performed;
    at least one statistical analysis of the results of the coincidence analysis is performed, and/or the results are subjected to a threshold analysis;
    said statistical analysis or at least one combination of several statistical analyses is evaluated for the presence of properties characteristic of an association, dissociation, linking or cleaving reaction or conformational change.

2. The method according to claim 1, characterized in that said time channel widths are greater than the longest fluorescence lifetime of said at least two dyes.

3. The method according to claim 1, characterized in that said time channel widths are smaller than the time required for said at least one sample molecule to pass through the measuring volume.

4. The method according to claim 1, characterized in that said detection units have different spectral detection sensibilities.

5. The method according to claim 1, characterized in that said measuring volume element V is $\leq 10^{-12}$ l.

6. The method according to claim 1, characterized in that said sample is illuminated by at least one laser which emits electromagnetic radiation of at least one wavelength which is capable of exciting said at least two dyes.

7. The method according to claim 1, characterized in that said coincidence analysis is performed on-line.

8. The method according to claim 1, characterized in that the time for performing the respective measurement is individually adjusted during the measurement.

9. The method according to claim 1, characterized in that the coincidence is established in the coincidence analysis by the amplitude G(0) of the cross-correlation.

10. The method according to claim 1, characterized in that the coincidence is established in the coincidence analysis through a logical AND switching operation.

11. The method according to claim 1, characterized in that the coincidence is established by multiplication according to the following formula:

$$K_i(n) = \frac{\sum_m \prod_j N(m, j)}{\prod_j \sum_m N(m, j)} \cdot n^{(i-1)}$$

wherein N(m,j) is the number of photons in time segment m of detector j; i is the total number of detection units employed; and n is the number of time segments within the time track.

12. The method according to claim 1, characterized in that the sample volume and the measuring volume are moved relative to one another.

13. The method according to claim 1, characterized in that systems are examined in which particles occur the molecular weights of which are different by less than a factor of two.

* * * * *